(12) United States Patent
Tilg et al.

(10) Patent No.: US 6,379,934 B1
(45) Date of Patent: Apr. 30, 2002

(54) PROCESS FOR THE FERMENTATIVE PREPARATION OF L-AMINO ACIDS USING CORYNEFORM BACTERIA

(75) Inventors: Yvonne Tilg, Mettmann; Bernd Eikmanns, Ulm; Lothar Eggeling; Hermann Sahm, both of Julich; Bettina Mockel, Bielefeld; Walter Pfefferle, Halle, all of (DE)

(73) Assignee: Degussa AG, Dusseldorf (DE)

( * ) Notice: Subject to any disclaimer, the term of this patent is extended or adjusted under 35 U.S.C. 154(b) by 0 days.

(21) Appl. No.: 09/363,389

(22) Filed: Jul. 29, 1999

(30) Foreign Application Priority Data

May 27, 1999 (DE) .......................... 199 24 364

(51) Int. Cl.[7] .......................... C12P 13/04; C12P 13/20; C12P 13/12; C12P 13/08; C12P 13/06
(52) U.S. Cl. .................. 435/106; 435/109; 435/113; 435/115; 435/116; 435/189; 435/232; 435/252.3; 435/252.31; 435/320.1
(58) Field of Search .................... 435/106, 115, 435/189, 232, 252.3, 252.31, 320.1, 109, 113, 116

(56) References Cited

U.S. PATENT DOCUMENTS 4,560,654 A    12/1985   Miwa et al.

FOREIGN PATENT DOCUMENTS

| DE | 38 23 451 | 1/1990 |
| EP | 0088166 A2 * | 9/1983 |
| EP | 358 940 | 3/1990 |
| EP | 387 527 | 9/1990 |

OTHER PUBLICATIONS

Jager et al. A C. glutamicum gene encoding two–domain protein similar to biotin carboxylases and biotin–carboxyl-–carrier proteins. Arch. Microbiol. 166:76–82, 1996.*

Oh et al. Improved L–lysine production by amplification of C. glutamicum dapA gene encoding Dihydropicolinate synthetase in E. coli. Biotech. Lett. vol. 13(10): 727–732, 1991.*

Perez, Carlos A. et al., "Effects on Bacillus subtilis of conditional expression of the accBC operon encoding subunits of acetyl coenzyme A carboxylase, the first enzyme of fatty acid synthesis," Microbiology (Reading), Bd. 144, Nr. 4, Apr. 1988, Seiten 895–903, XP000946310.

Jaeger, Wolfgang et al., "A Corynebacterium glutamicum gene encoding a two–domain protein similar to biotin carboxylases and biotin–carboxyl–carrier proteins," Archives of Microbiology, BD 166, Nr. 2, 1996, Seiten 76–82, XP000946309.

* cited by examiner

Primary Examiner—Rebecca E. Prouty
Assistant Examiner—Manjunath N. Rao

(57) ABSTRACT

The invention provides a process for the fermentative preparation of L-amino acids using coryneform bacteria, in which the subunit carrying the biotin-carboxyl carrier protein domain and the biotin-carboxylase domain of the nucleotide sequence encoding the enzyme acetyl-CoA carboxylase (accBC gene) is amplified, in particular is overexpressed.

10 Claims, 1 Drawing Sheet

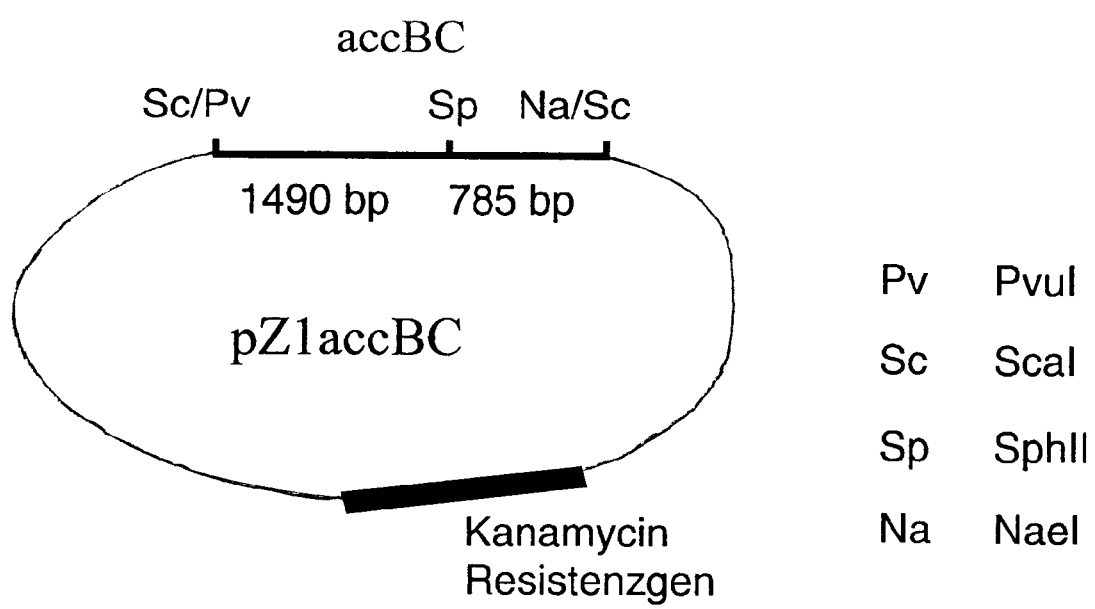

PROCESS FOR THE FERMENTATIVE PREPARATION OF L-AMINO ACIDS USING CORYNEFORM BACTERIA

CROSS REFERENCE TO RELATED APPLICATIONS

The present application claims priority under 35 U.S.C. § 119 to German application 199 24 364.6, filed on May 27, 1999.

The invention provides a process for the fermentative preparation of L-amino acids, in particular lysine, using coryneform bacteria in which the accBC gene is amplified.

Prior Art

L-amino acids, in particular L-lysine, are used in animal nutrition, in human medicine and in the pharmaceutical industry.

It is known that these amino acids are prepared by fermentation using strains of coryneform bacteria, in particular Corynebacterium glutamicum. Due to the high degree of importance of these products, a constant effort is made to improve the method of preparation. Process improvements may be based on fermentation engineering steps such as, for example, stirring and supplying with oxygen, or the composition of the nutrient medium such as, for example, the concentration of sugar during fermentation, or the working up process aimed at obtaining the product itself by, for example, ion-exchange chromatography or the intrinsic power of the microorganism itself.

The methods of mutagenesis, selection and mutant choice are used to improve the power of these microorganisms. Strains which are resistant to antimetabolites such as, for example, the lysine analogon S-(2-aminoethyl)-cysteine or which are auxotrophic for significant regulatory amino acids, and produce L-amino acids, are obtained in this way.

For some time now the methods of recombinant DNA engineering have also been used for the strain-improvement of L-amino acid producing strains of Corynebacterium glutamicum, by amplifying individual amino acid biosynthetic genes and investigating the effect on L-amino acid production. Review articles about this topic can be found, inter alia, in Kinoshita ("Glutamic Acid Bacteria", in: Biology of Industrial Microorganisms, Demain and Solomon (Eds.), Benjamin Cummings, London, UK, 1985, 115–142), Hilliger (BioTec 2, 40–44 (1991)), Eggeling (Amino Acids 6, 261–272 (1994)), Jetten and Sinskey (Critical Reviews in Biotechnology 15, 73–103 (1995)) and Sham et al. (Annuals of the New York Academy of Science 782, 25–39 (1996)).

Object of the Invention

The inventor has formulated the object as the provision of new steps for the improved fermentative preparation of L-amino acids, in particular L-Lysine.

DESCRIPTION OF THE INVENTION

L-amino acids, in particular L-lysine, are used in animal nutrition, in human medicine and in the pharmaceuticals industry. There is, therefore, general interest in the provision of new, improved methods for preparing these compounds.

Whenever L-lysine or lysine is mentioned in the following, this is intended to mean not only the base but also salts such as, for example, lysine monohydrochloride or lysine sulfate.

The invention provides a process for the fermentative preparation of L-amino acids, in particular L-lysine, using coryneform bacteria which in particular already produce the desired amino acid and in which the subunits carrying the biotin-carboxyl carrier protein domain and the biotin-carboxylase domain in the nucleotide sequence encoding the enzyme acetyl-CoA carboxylase is amplified, in particular is overexpressed.

Preferred embodiments are given in the Claims.

The expression "amplification" in this connection describes the increase in the intracellular activity of one or more enzymes in a microorganism which are encoded by the corresponding DNA, for example by increasing the copy number of the gene or by using a strong promoter or a gene which encodes for a corresponding enzyme with high activity and optionally combining these measures.

The microorganisms which are the object of the present invention can produce L-amino acids, in particular L-lysine from glucose, saccharose, lactose, fructose, maltose, molasses, starch, cellulose or from glycerol and ethanol. They are members of the group of coryneform bacteria, in particular those of the genus Corynebacterium. With regard to the genus Corynebacterium, in particular the species Corynebacterium glutamicum, it should be mentioned that this is well-known in the specialist field for its ability to produce L-amino acids.

Suitable strains of the genus Corynebacterium, in particular the species Corynebacterium glutamicum, are the recognized wild strains Corynebacterium glutamicum ATCC13032
Corynebacterium acetoglutamicum ATCC15806
Corynebacterium acetoacidophilum ATCC13870
Corynebacterium thermoaminogenes FERM BP-1539
Brevibacterium flavum ATCC14067
Brevibacterium lactofermentum ATCC13869 and
Brevibacterium divaricatum ATCC14020 and the mutants and strains prepared therefrom which can produce L-amino acids, in particular L-lysine, such as, for example Corynebacterium glutamicum FERM-P 1709
Brevibacterium flavum FERM-P 1708
Brevibacterium lactofermentum FERM-P 1712
Brevibacterium flavum FERM-P 6463 and
Brevibacterium flavum FERM-P 6464.

The accBC gene encodes for a subunit of acetyl-CoA carboxylase which carries a biotin-carboxyl carrier protein domain and a biotin-carboxylase domain. The nucleotide sequence of the accBC gene in Corynebacterium glutamicum was determined by Jäger et al. (Archives of Microbiology 166, 76–82 (1996)) and it is generally available at the Databank of the European Molecular Biology Laboratories (EMBL, Heidelberg, Germany) under Accession Number U35023.

The accBC gene of C. glutamicum described by Jäger et al. (Archives of Microbiology 166, 76–82 (1996)) can be used in accordance with the invention. Furthermore, alleles of the accBC gene which are produced as a result of the degenerativeness of the genetic code or by function-neutral sense mutations can also be used.

To produce an overexpression, the copy number of the corresponding gene can be increased or the promoter and regulation region or the ribosome bonding site, which are located upstream of the coding sequence, can be mutated. Expression cassettes, which are incorporated upstream of the coding sequence, operate in the same way. It is also possible to increase expression during the course of fermentative L-lysine production with inducible promoters. Expression is also improved by measures aimed at prolonging the lifetime of m-RNA. Furthermore, enzyme activity can also be amplified by inhibiting degradation of the enzyme protein. The genes or gene constructs may either be present in plasmids with different copy numbers or be integrated and amplified in the chromosome. Alternatively, overexpression of the genes concerned may also be achieved by modifying the composition of the media and management of the culture.

Instructions for these procedures may be found by a person skilled in the art in, inter alia, Martin et al. (Bio/Technology 5, 137–146 (1987)), in Guerrero et al. (Gene 138, 35–41 (1994)), Tsuchiya and Morinaga (Bio/Technology 6, 428–430 (1988), in Eikmanns et al. (Gene 102, 93–98 (1991)), in European Patent EP-B 0 472 869, in U.S. Pat. No. 4,601,893, in Schwarzer and Puhler (Bio/Technology 9, 84–87 (1991), in Reinscheid et al. (Applied and Environmental Microbiology 60, 126–132 (1994)), in LaBarre et al. (Journal of Bacteriology 175, 1001–1007 (1993)), in Patent Application WO 96/15246, in Malumbres et al. (Gene 134, 15–24 (1993)), in Japanese Patent JP-A-10–229891, in Jensen and Hammer (Biotechnology and Bioengineering 58, 191–195 (1998)), in Makrides (Microbiological Reviews 60:512–538 (1996)) and in well-known textbooks relating to genetics and molecular biology.

An example of a plasmid with the aid of which the accBC gene can be overexpressed is pZ1accBC (FIG. 1), which is contained within the strain MH20–22B/pZ1accBC. Plasmid pZ1accBC is an E.coli—C. glutamicum shuttle vector based on Plasmid pZ1 (Menkel et al., Applied and Environmental Microbiology 55(3), 684–688 (1989)) which carries the accBC gene.

In addition, it may be advantageous for the production of L-amino acids to overexpress one or more enzymes in the corresponding biosynthetic pathway, in addition to the accBC gene. Thus, for example, when preparing L-lysine
   the dapA gene encoding for dihydrodipicolinate synthase can be simultaneously overexpressed (EP-B 0 197 335), or
   a S-(2-aminoethyl)-cysteine-resistance promoting DNA fragment can be simultaneously amplified (EP-A 0 088 166).

Furthermore, it may be advantageous for the production of L-amino acids if, in addition to overexpression of the accBC gene, undesired side-reactions are switched off (Nakayama: "Breeding of Amino Acid Producing Microorganisms", in: Overproduction of Microbial Products, Krumphanzl, Sikyta, Vanek (eds.), Academic Press, London, UK, 1982).

Microorganisms prepared according to the invention may be cultivated continuously or batchwise in a batch process or a fed batch or repeated fed batch process for the purposes of producing L-amino acids. A summary of known methods of cultivation is described in the textbook by Chmiel (Bioprozesstechnik 1. Einfuhrung in die Bioverfahrenstechnik (Gustav Fischer Verlag, Stuttgart, 1991)) or in the textbook by Storhas (Bioreaktoren und periphere Einrichtungen (Vieweg Verlag, Braunschweig/Wiesbaden, 1994)).

The culture medium being used must satisfy the requirements of the particular strain in a suitable manner. Descriptions of culture media for various microorganisms can be found in the book "Manual of Methods for General Bacteriology" by the American Society for Bacteriology (Washington D.C., USA, 1981). Sources of sugar which may be used are sugar and carbohydrates such as e.g. glucose, saccharose, lactose, fructose, maltose, molasses, starch and cellulose, oils and fats such as e.g. soy oil, sunflower oil, groundnut oil and coconut oil, fatty acids such as e.g. palmitic acid, stearic acid and linoleic acid, alcohols such as e.g. glycerol and ethanol and organic acids such as e.g. acetic acid. These substances may be used individually or as mixtures. Sources of nitrogen which may be used are organic nitrogen-containing compounds such as peptones, yeast extract, meat extract, malt extract, maize steep liquor, soy bean meal and urea or inorganic compounds such as ammonium sulfate, ammonium chloride, ammonium phosphate, ammonium carbonate and ammonium nitrate. The sources of nitrogen may be used individually or as mixtures. Sources of phosphorus which may be used are potassium dihydrogen phosphate or dipotassium hydrogen phosphate or the corresponding sodium-containing salts. Furthermore, the culture medium must contain salts of metals, such as e.g. magnesium sulfate or iron sulfate, which are needed for growth. Finally, essential growth substances such as amino acids and vitamins may be used in addition to the substances mentioned above. Over and above these, suitable precursors may also be added to the culture medium. The feedstocks mentioned may be added to the culture in the form of a one-off batch or may be fed during the cultivation procedure in a suitable manner.

Basic compounds such as sodium hydroxide, potassium hydroxide, ammonia or acid compounds such as phosphoric acid or sulfuric acid may be used in a suitable manner to regulate the pH of the culture. Anti-foam agents such as e.g. fatty acid polyglycol esters may be used to control the production of foam. Appropriate selectively acting substances, e.g. antibiotics, may be added to the medium in order to maintain stability of the plasmids. In order to maintain aerobic conditions, oxygen or oxygen-containing gas mixtures such as e.g. air are introduced into the culture. The temperature of the culture is normally 20° C. to 45° C. and preferably 25° C. to 40° C. The culture procedure is continued until a maximum amount of the desired L-amino acid has been produced. This target is normally achieved within 10 hours to 160 hours.

L-amino acids can be analyzed by anion exchange chromatography and subsequent ninhydrin derivatization as described, for example, in Spackman et al. (Analytical Chemistry, 30, (1958), 1190).

The Corynebacterium glutamicum strain DSM5715/pZ1accBC was deposited at the German Collection of Microorganisms and Cultures (Braunschweig, Germany) under the number DSM 12786 in accordance with the Budapest treaty.

The process according to the invention is used for the fermentative preparation of L-amino acids, in particular L-aspartic acid, L-asparagine, L-homoserine, L-threonine, L-isoleucine und L-methionine using coryneform bacteria, in particular the preparation of L-lysine.

EXAMPLES

The present invention is described in more detail in the following, using specific examples.

For this purpose, trials were performed with the L-lysine-producing strain DSM5715, (EP-B- 0 435 132), in which the superiority of the claimed process is demonstrated:

Example 1

Preparing the expression plasmid pZ1accBC and the strain DSM5715/pZ1accBC

To construct the expression plasmid pZ1accBC, the accBC gene-containing plasmid pWJ71 (Jäger et al., Archives of Microbiology (1996) 166:76–82) was digested with the restriction enzymes PvuI and NaeI and then treated with Klenow polymerase and alkaline phosphatase. The 2.1 kpb DNA fragment bearing the accBC gene was isolated by preparative isolation from an agarose gel, this being performed in the way described in Sambrook et al. (Molecular Cloning a Laboratory Manual (1989) Cold Spring Harbour Laboratories). In parallel to preparation of the accBC gene, the plasmid pZ1 (Menkel et al., Applied and Environmental Microbiology 55(3), 684–688 (1989)) was digested with the restriction enzyme ScaI and then treatment with Klenow polymerase and alkaline phosphatase was also performed. The prepared accBC gene and the vector pZ1, treated in the way described above, were ligated and the strain DSM5715 was transformed with the ligation mixture in the way described in Liebl et al. (FEMS Microbiology Letters 65, 299–304 (1989)). The transformants were selected on brain/heart agar from the Merck Co. (Darmstadt, Germany), which had been supplemented with 50 mg/l of kanamycin. One selected transformant was called strain DSM5715/pZ1accBC. The restriction chart for the expression plasmid pZ1accBC is shown in FIG. 1.

Example 2

Preparation of L-lysine

The strain DSM5715/pZ1accBC was pre-cultivated in complete medium CgIII (Kase & Nakayama, Agricultural and Biological Chemistry 36 (9) 1611–1621 (1972)) which had been supplemented with 50 jg/ml of kanamycin. For this purpose, 10 ml of medium CgIII, which was contained in 100 ml conical flasks with 4 baffles, was inoculated with an inoculant of the strain and the culture was incubated for 16 hours at 240 rpm and 30° C.

The OD (optical density) (660 nm) of the pre-culture was determined in order to inoculate 10 ml of production medium, which was contained in 100 ml conical flasks with 4 baffles. The main culture which contained the production medium was inoculated to an OD of 0.1. The medium CgXII described by Keilhauer et al., (Journal of Bacteriology 175: 5595–5603 (1993)) was used as the production medium. 4% of glucose and 50 mg/l of kanamycin sulfate were added. The cells were incubated at 33° C., 250 rpm and 80% humidity for 48 hours.

In the process using the strain DSM5715 the corresponding media contained no kanamycin.

Finally, the optical density at 660 nm and the concentration of L-lysine produced were determined using an amino acid analyzer from the Eppendorf-BioTronik Co. (Hamburg, Germany) by ion exchange chromatography and post-column reaction with ninhydrinane detection. The results of the trials are given in table 1.

TABLE 1

| Strain | OD | L-lysine g/l |
|---|---|---|
| DSM5175 | 31.4 | 7.2 |
| DSM5715/pZ1accBC | 27.6 | 9.6 |

The following figure is attached:

FIG. 1: Chart of the plasmid pZ1accBC.

What is claimed is:

1. A process for preparing L-amino acids by the fermentation of coryneform bacteria, wherein
bacteria are cultured in which the nucleotide sequence of the accBC gene is amplified.

2. A process as claimed in claim 1, wherein
bacteria are used in which the metabolic pathways which reduce production of the desired L-amino acid are at least partly repressed.

3. A process as claimed in claim 1, wherein
a strain which has been transformed with a plasmid vector is used and the plasmid vector accBC gene.

4. A process as claimed in claim 3, wherein
Corynebacterium glutamicum bacteria, deposited under the number DSM 12786, transformed with the plasmid vector pZ1accBC and shown in FIG. 1 are used.

5. A process as claimed in claim 1, wherein
coryneform bacteria which produce L-aspartic acid, L-asparagine, L-homoserine, L-threonine, L-isoleucine or L-methionine are used.

6. A process as claimed in one of claims 1 to 4, wherein
coryneform bacteria which produce L-lysine are used.

7. A process as claimed in claim 6, wherein
the dapA gene coding for dihydrodipicolinate synthase is simultaneously overexpressed.

8. A process as claimed in claim 6, wherein
a S-(2-aminoethyl)-cysteine resistance-promoting DNA-fragment is simultaneously amplified.

9. A process for the fermentative preparation of L-amino acids in accordance with claim 1, wherein
the following steps are performed
a) fermentation of the bacteria producing the desired L-amino acid, in which at least the accBC gene is amplified,
b) enrichment of the L-amino acid in the medium or in the cells of the bacteria and
c) isolation of the L-amino acid produced.

10. The process of claim 1 wherein the nucleotide sequence is overexpressed.

* * * * *

UNITED STATES PATENT AND TRADEMARK OFFICE
CERTIFICATE OF CORRECTION

PATENT NO. : 6,379,934 B1
DATED : April 30, 2002
INVENTOR(S) : Tilg et al

It is certified that error appears in the above-identified patent and that said Letters Patent is hereby corrected as shown below:

<u>Title page,</u>
Item [75], Inventors: please change name of $2^{nd}$ inventor from "Bernd Eikmanns" to -- Bernhard Eikmanns --.

Signed and Sealed this

Twenty-second Day of October, 2002

Attest:

Attesting Officer

JAMES E. ROGAN
*Director of the United States Patent and Trademark Office*